United States Patent [19]

Boeck

[11] Patent Number: 4,829,991

[45] Date of Patent: May 16, 1989

[54] METHOD AND DEVICE FOR STIMULATING AN ERECTION

[75] Inventor: Robert F. Boeck, Racine, Wis.

[73] Assignee: Medical Engineering Corp., Racine, Wis.

[21] Appl. No.: 628

[22] Filed: Jan. 6, 1987

[51] Int. Cl.$^4$ .............................................. A61F 5/41
[52] U.S. Cl. ....................................... 128/79; 128/844
[58] Field of Search ............... 128/79, 138 R, 132 R, 128/844; 604/289, 304, 308, 347; 514/929

[56] References Cited

U.S. PATENT DOCUMENTS

| | | | |
|---|---|---|---|
| 3,363,624 | 1/1968 | Fishman | 128/79 |
| 3,699,963 | 10/1972 | Zaffaroni | 604/897 |
| 4,421,737 | 12/1983 | Ito et al. | 604/897 |
| 4,569,343 | 2/1986 | Kimura et al. | 604/897 |
| 4,576,156 | 3/1986 | Dyck et al. | 128/138 R |
| 4,619,654 | 10/1986 | Abplanalp | 604/897 |
| 4,627,429 | 12/1986 | Lsuk | 604/897 |
| 4,650,484 | 3/1987 | Shaw et al. | 604/897 |
| 4,661,105 | 4/1987 | Gale | 604/897 |
| 4,675,009 | 6/1987 | Hymes et al. | 604/897 |

Primary Examiner—Gene Mancene
Assistant Examiner—Cary E. Stone
Attorney, Agent, or Firm—Stuart E. Krieger

[57] ABSTRACT

A condom is coated on the interior surface with a vasoactive coating, such as a transdermal nitroglycerine coating. As the comdom is fitted onto a penis, contact between the penile tissue and the transdermal nitroglycerine coating increases blood flow through the corpus cavernosum. The resulting increase in blood flow aids the development of a tumescent condition of the penis.

13 Claims, 1 Drawing Sheet

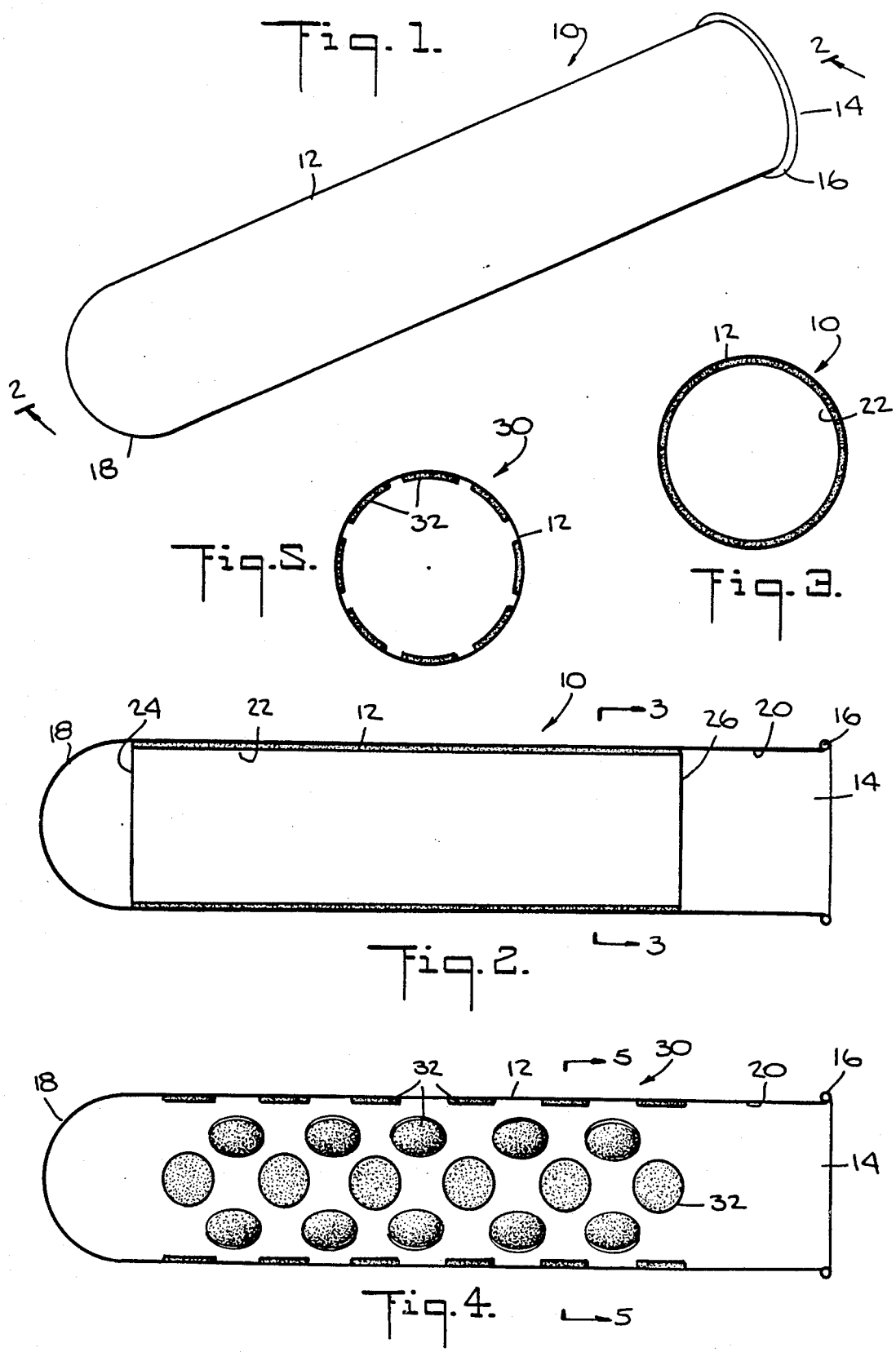

METHOD AND DEVICE FOR STIMULATING AN ERECTION

BACKGROUND OF THE INVENTION

This invention relates to devices and methods for producing an erectile condition, and more particularly to a prophylactic device and method for stimulating an erection.

It is well known that the inability of some males to reach an erectile condition may be due to psychological factors, physiological factors or a combination of both. This invention deals with the problems of impotency wherein the afflicted individual is physically capable of having an erection but has difficulty reaching and/or maintaining an erection for purposes of sexual intercourse. Thus, the term impotency as used herein is intended to refer to the inability to reach and/or maintain an erectile condition by individuals who are otherwise physically capable of having an erection.

One of the devices which addresses the problem of male impotency, as shown in U.S. Pat. No. 4,127,118, includes a specially designed syringe for injecting a vasodilator into the penis. The use of this device can be somewhat uncomfortable or painful, as well as frightening to some, and occasionally difficult to manipulate. U.S. Pat. No. 3,363,624 discloses a method for prolonging an erectile condition by use of a desensitizing agent applied to the closed end of a condom. This patent deals with the problem of premature ejaculation and maintaining the duration of an erection but does not address the problem of producing an erection for those individuals who have difficulty reaching the erectile state.

It is thus desirable to provide a method and device for stimulating and maintaining an erection which does not require injections and does not require any special operational procedures other than the use of a condom.

OBJECTS AND SUMMARY OF THE INVENTION

Among the several objects of the invention may be noted the provision of a novel device for stimulating and maintaining an erection, an novel prophylactic device for stimulating and maintaining an erection, a novel prophylactic device having an interior surface coated with a vasodilator, and a novel method for stimulating and maintaining an erection.

Other objects and features of the invention will be in part apparent and in part pointed out hereinafter.

In accordance with the present invention, a prophylactic device, such as a condom, is provided with a vasodilator coated on the interior surface except at the open and closed end portions of the condom. The vasodilator can include a transdermal nitroglycerine coating which is applied uniformly on the inner portion of the condom or applied sporadically throughout most of the condom except at the open and closed end portions. The open end of the condom would be free of any transdermal coating for the first one-half to one inch.

As the condom is fitted onto the penis, the friction between the penis and the condom results in a breaking of the surface tension of the transdermal nitroglycerin coating. The transdermal nitro coating thus makes contact with the penile skin resulting in the gradual development of an erectile condition which facilitates a more complete insertion of the penis into the condom. Once the penis is fully inserted into the condom, there is optimum contact between the penile tissue and the transdermal nitroglycerin coating.

The transdermal nitroglycerin coating enables the individual to obtain and sustain an erection sufficient to achieve intercourse.

The invention accordingly comprises the constructions and method hereinafter described, the scope of the invention being indicated in the claims.

DESCRIPTION OF THE DRAWINGS

In the accompanying drawing in which several embodiments of the invention are illustrated, FIG. 1 is a simplified perspective view of one embodiment of the prophylactic device used for stimulating and maintaining an erection;

FIG. 2 is a sectional view taken on the line 2—2 of FIG. 1;

FIG. 3 is a sectional view taken on the line 3—3 of FIG. 2;

FIG. 4 is a sectional view of another embodiment of the invention; and,

FIG. 5 is a sectional view taken on the line 5—5 of FIG. 4.

Corresponding reference characters indicate corresponding parts throughout the several views of the drawing.

DETAILED DESCRIPTION OF THE INVENTION

A prophylactic device incorporating one embodiment of the invention is generally indicated by the reference number 10 of FIG. 1.

The prophylactic device 10 comprises a condom 12, which can be formed of latex in any suitable known manner. The condom 12 includes an open end 14 having a rim portion 16 and an opposite closed end 18. The condom 12 has an interior surface 20 which extends from the open end 14 to the closed end 18.

A portion of the interior surface 20 is coated with a transdermal nitroglycerin coating 22 such as the type sold under the same Nitroglycerin Transdermal by Ciba-Geigy or Nitro-Disc sold by Searle. The transdermal nitroglycerin coating 22 extends from approximately one-half to one inch from the rim 16 to a point just before the curved closed end portion 18 of the condom 12 so as to avoid contact of the nitroglycerin with the urethral meatus. The uncoated portions of the interior surface 20 can be masked or otherwise covered before the coating 22 is applied. The coating 22 can be applied by spraying, brushing or use of a coated mandril (not shown).

Once the coating 22 is applied, the condom 12 is packaged in a suitable known airtight foil wrapper or plastic container (not shown). Preferably the rim 16 of the condom 12 is not rolled toward the end portion 18. Rather, the condom 12 can be folded upon itself in accordion fashion, with one of the fold lines being represented by an end portion 24 of the coating 22 and an end portion 26 of the coating 22 (FIG. 2).

In using the prophylactic device 10, the condom 12 is fitted onto the penis (not shown) by grasping the rim 16 and inserting the penis into the interior space of the condom in a manner similar to that used with a conventional condom.

As the penile tissue contacts the transdermal nitroglycerin coating 22, the flow of blood through the corpus cavernosum increases the a gradual buildup of the tumescent condition results.

If desired, a light coating of a lubricant such as vaseline petroleum jelly can be applied to the urethral meatus before the condom is applied to minimize contact of the coating 22 with the urethral meatus.

Another embodiment of the prophylactic device is generally indicated by the reference number 30 in FIG. 4.

The prophylactic device 30 includes a condom 12 of the type previously described. However, the interior surface 20 is coated sporadically with a transdermal nitroglycerin coating 32 in small areas. Although the small areas are shown as circular, they can be of any shape or form. Uncoating portions of the inner surface 20 are also present in the prophylactic device 30 at the closed end 18 and the open end 14. Use of the prophylactic device 30 is similar to that described for the prophylactic device 10.

Some advantages of the present invention evident from the foregoing description include a device for stimulating and maintaining an erection which requires no special skills or procedures to use. The novel device is painless, nonpermanent in its effect, and can be used without apprehension, since no pain is associated with the device.

The device presents a novel method for producing and maintaining an erection, by providing a vasodilator coating to the inner surface of a condom thereby stimulating an erection as the condom is applied to the penis.

In view of the above, it will be seen that the several objects of the invention are achieved and other advantageous results attained.

As various changes can be made in the above constructions and method without departing from the scope of the invention, it is intended that all matter contained in the above description or shown in the accompanying drawing shall be interpreted as illustrative and not in a limiting sense.

What is claimed is:

1. A device for stimulating and maintaining an erection comprising, an elastic sleeve-like member which is predeterminedly dimensioned so as to fit onto a penis, said sleeve-like member having an interior surface, and a vasoactive dilator coating on said interior surface for contacting penile tissue and stimulating tumescence when said sleeve-like member is fitted onto the penis.

2. The device as claimed in claim 1, wherein said sleeve-like member comprises a condom.

3. The device as claimed in claim 1, wherein said condum has a closed end portion and an open end portion and said vasoactive dilator coating terminates approximately ½ to 1 inch before said open end portion and terminates before said closed end portion.

4. The device as claimed in claim 1, wherein said vasoactive dilator coating has a sporadic pattern.

5. The device as claimed in claim 1, wherein said vasoactive dilator coating includes nitroglycerine.

6. The device as claimed in claim 1, wherein said vasoactive dilator coating is a transdermal nitroglycerine coating.

7. The device as claimed in claim 6, wherein said transdermal nitroglycerine coating is applied in patches.

8. A method of stimulating and maintaining an erection comprising:
    (a) predeterminedly dimensioning a sleeve-like elastic member to fit onto a penis;
    (b) coating the interior surface of said sleeve-like elastic member with a vasoactive dilator coating;
    (c) fitting said sleeve-like elastic member onto a penis; and
    (d) contacting the penile tissue with the vasoactive coating to help stimulate tumescene and produce and erection.

9. The method of claim 8, wherein the vasoactive coating is a transdermal nitroglycerine coating.

10. The method of claim 8 wherein said elastic sleeve-like member is a condom.

11. The method of claim 10, wherein the vasoactive coating is applied intermediate the closed end of the condom and the open end of the condom.

12. The method of claim 10, wherein the vasoactive coating is sporadically applied to the inner surface of the condom.

13. The method of claim 10, wherein the vasoactive coating is uniformly applied to the interior surface of the condom.

* * * * *